United States Patent [19]

Harris

[11] Patent Number: 4,585,444
[45] Date of Patent: Apr. 29, 1986

[54] INTRAVENOUS NEEDLE ASSEMBLY

[75] Inventor: Christopher Harris, Redditch, England

[73] Assignee: Smith and Nephew Associated Companies Limited, London, England

[21] Appl. No.: 477,805

[22] Filed: Mar. 22, 1983

[51] Int. Cl.⁴ .............................................. A61N 5/00
[52] U.S. Cl. .................................................... 604/177
[58] Field of Search .............. 604/177, 174, 180, 165; 128/DIG. 26

[56] References Cited

U.S. PATENT DOCUMENTS

| | | | |
|---|---|---|---|
| 3,537,451 | 11/1970 | Beck et al. | 604/165 |
| 4,192,304 | 3/1980 | Millet | 604/177 X |
| 4,326,519 | 4/1982 | D'Alo et al. | 604/177 X |
| 4,388,074 | 6/1983 | Seberg et al. | 604/177 X |

Primary Examiner—Stephen C. Pellegrino
Attorney, Agent, or Firm—F. Rhett Brockington

[57] ABSTRACT

A handle for use in an intravenous needle assembly in which the handle comprises a body portion being connected via hinge portions to oppositely extending wing sections. The body portion of the handle has at its distal end an insertion aid in the form of laterally extending horns against which pressure may be applied when introducing the point of the needle of the intravenous needle assembly which comprises a needle, a hub which rigidly holds the needle and a handle as described above which is mounted on the needle hub in a manner which allows free rotation of the needle hub within the handle.

2 Claims, 7 Drawing Figures

INTRAVENOUS NEEDLE ASSEMBLY

The present invention relates to an intravenous needle assembly for placing and maintaining an intravascular needle within a vein.

Intravenous needle assemblies of the general type with which the present invention is concerned are known in the art. Examples of such prior art assemblies are described in, for example, U.S. Pat. Nos. 2,725,058, 3,064,648, 3,640,275, 3,782,383, 4,015,600, British Pat. Nos. 1257639, 1274179, 1279852, European Patent Application No. 0033207 and International Application No. WO 81/01518. A variety of devices are commercially available. However the presently available devices show certain deficiencies and disadvantages. Most prior art devices include a handle comprising a pair of oppositely extending wings connected via a hinge or weakened section to a wing hub which rigidly holds a pointed hollow needle. To insert a needle into the vein beneath the skin the wings are folded together and grasped by the fingers and thumb. As a result the forward pressure applied to the needle to push it through the skin is applied above and behind the needle. If the material forming the handle is flexible the needle may be easily diverted from its path, for example by tough skin. If the material is rigid the fingers may slip if the handle is wet or contaminated by lubricant. Such rigid material may also make more difficult the positioning of the point of the needle after it has punctured the skin. The present device mitigates this deficiency by providing on the handle of the assembly an insertion aid, preferably in the form of a pair of oppositely extending horns against which the finger and thumb grasping the handle may apply positive pressure during insertion. This provides a rigid handle which is less likely to be diverted by tough skin or to allow the fingers to slip if wet. The handle also allows better accuracy when positioning the point of the needle. A preferred embodiment in which the wing portions of the handle fit around the body portion when folded further enhances these advantages.

If the needle when in position should become blocked or lodged with the bevel of the point against the wall of the vein, it is known that mere rotation of the needle within the vein will free the needle from obstruction and restore relatively free flow of fluid. A disadvantage of present devices in which the needle is fixed rigidly to the wing assembly, is that wing assembly must be untaped or unstuck from the skin, the whole assembly rotated and then retaped or readhered. Even those assemblies which have only a single wing must be untaped and rotated through 180° and then retaped. Such operations may cause unexpected movement which may damage the vein of the patient. The assemblies envisaged in a preferred embodiment of the present invention will allow free rotation of the needle and its hub within the body portion of the handle, thereby allowing unblocking of the needle without inconvenience and at reduced risk to the patient. Therefore the intravenous needle assembly of the present invention will improve handling by the physician, facilitate insertion of the needle by ensuring efficient application of applied forces in the intended direction, will sit comfortably on the skin and will in a preferred embodiment enable rotational manipulation of the needle if desired without disturbing the taping site.

Accordingly the present invention provides a handle for use in an intravenous needle assembly which comprises a body portion being connected via hinge portions to oppositely extending wing sections characterised in that the body portion has at its distal end an insertion aid against which pressure may be applied when introducing the point of the needle assembly beneath the skin.

Suitably the insertion aid will take the form of laterally extending horns.

Preferably the insertion aid is in the form of a pair of laterally extending horns.

Suitably each horn will extend away from the axis of the needle such that the angle between the direction of the horn and the axis of the needle lies between 20° and 90° and preferably lies between 30° and 60°.

The length of the horns will depend upon the overall size of the intravenous needle assembly but generally they will be between 1.5 to 10 mm in length, more suitably will be 2.0 to 7.5 mm and preferably will be 2.5 to 5.0 mm in length.

Aptly the horns will be straight or arcuate in shape. Preferably the horns will be straight.

In a second embodiment each wing section of the handle has adjacent to the hinge a thinner portion of such dimension that when the wings are folded, the thinner portion conforms and folds around the body portion in close fit therewith. This provides greater stability to the needle and handle in relation to the forward pressure exerted on them during insertion.

In a second aspect therefore the present invention provides a handle for use in an intravenous needle assembly which comprises a body portion being connected via hinge portions to oppositely extending wing sections characterised in that each wing section has adjacent to the hinge a thinner portion of such dimension that when the wings are folded, the thinner portion conforms and folds around the body portion in close fit therewith.

In a preferred version of this aspect the thinner portions have on their surface raised areas so that when the wings are folded the raised areas contact the body portion and thereby increase the pressure applied to the walls of the body portion. Suitably the raised areas may be in the form of a pattern or may be in the form of a single raised line, preferably of triangular cross-sectional area. The raised areas will normally not cover more than 50% of the thinner portion.

In a particularly preferred aspect the horns and wings with thinner portions will both be present in the handle. This has the advantage of allowing greater access of the finger and thumb to the horns as the wings are folded out of the way.

Suitably the body portion may be of circular or rectangular, including square, cross-section. Preferably the body portion is square in cross-section.

When folded the wing sections do not interlock or otherwise fit together as is found in several prior art devices, but may touch only at their tips. In the aspect of the invention in which the needle hub is free to rotate within the body portion, the folding of the wings causes stress in the body portion which results in a temporary distortion in the shape of the body which prevents the needle hub rotating. When the wings are unfolded to their normal flat position the needle hub is again free to rotate.

In a further aspect of the invention the surface of the wing area which is to contact the body portion when the wings are folded has raised areas which will cause the needle hub to be gripped more strongly than before when the wings are folded. Suitably the raised areas will be in the form of a pattern or may be in the form of a single raised line, preferably of triangular cross-section which runs from the front to the back of the handle. When the rasied areas are on a thinner portion of the wing area they will not cover, suitably, more than 50% of this area as this will reduce the flexibility of the thinner area and thereby make manipulation more difficult. Most preferably each thinner area will have a raised line of triangular cross-section which runs from the front to the back of the handle.

From the foregoing it is clear that the handle may form an integral part of the intravenous needle assemble, that is the blunt end of the needle may be held rigidly within the handle. However, in a preferred embodiment the handle is adapted to surround a needle hub which rigidly holds the needle in such a manner as to permit free rotation of the needle hub about its axis inside the handle.

Thus in another aspect the present invention comprises an intravenous needle assembly comprising a needle and a handle as hereinbefore described wherein the needle is rigidly held in the handle.

In a further more favoured aspect the present invention comprises an intravenous needle assembly comprising (a) a needle, (b) a hub and (c) a handle as hereinbefore described wherein the needle is rigidly mounted within the hub and the handle is mounted on the hub in a manner which allows free rotation of the needle hub within the handle, In either aspect the assembly may advantageously carry a connection tube closed by a luer lock at its distal end at the proximal end of the handle or hub respectively which forms a reusable connection to an extracorporeal blood circuit or source of infusion fluid and the like.

Generally the handle comprised of the body portion, wing section and insertion aid will be formed as a single unit by injection moulding from a thermoplastic polymer. Aptly the thermoplastic polymer will be a polyolefin. Suitable polyolefins include highdensity and lowdensity polyethylene and polypropylene. A preferred polyolefin is polypropylene. The polyolefins, and polypropylene in particular, have the advantage of being rigid whilst being capable of forming a hinge portion without becoming brittle on flexing. Such polymers wil reversibly accept stress which in the preferred embodiment allows the needle hub to be held still during insertion with the wing sections folded whilst allowing free rotation of the needle hub when relaxed. The polyolefins are hypoallergenic when used in contact with the skin. The polyolefins may be easily colour coded to designate different gauges of needle.

In general the pointed needle will be of the type conventionally used for intravenous applications. Suitably the needles are formed from stainless steel which optionally may be covered by a biocompatible coating to aid performance. Most aptly the outside diameter of the needles will be between 1.5 and 2.0 mm. When fixed within the needle hub, the exposed length of the needle will be between 15 to 35 mm and preferably is 25 to 30 mm.

In the embodiment wherein the needle is held rigidly in the handle, the handle is suitably moulded around the blunt end of the needle which has been previously roughened or scored to provide a keying surface. Alternatively the needle may be fixed in a preformed handle by the use of a suitable adhesive.

In the preferred embodiment the needle hub will be formed from methacrylate-butadiene-styrene polymer (known as MBS polymer) or acrylonitrile-butadiene-styrene polymer (known as ABS polymer). The ABS or MBS polymer is conventionally moulded around the needle to form the hub. The enclosed end of the needle is previously roughened or scored to ensure the needle is held fixedly in the hub. The internal bore of the needle and needle hub is arranged to be as smooth as possible to reduce to the minimum the risk of damage to infused fluids, for example, blood.

Suitably in this preferred embodiment the needle hub will have an annular flange close to its distal end. The body portion and wing sections are held between this flange and tubing which is sealed around the proximal end of the hub and which connects to the extracorporeal blood circuit or source of fluid to be infused. As described hereinbefore the body portion is free to rotate around the needle hub.

The tubing is aptly that which is commonly used for administration of fluid to the body. Suitably the tubing may be a polyvinyl chloride, silicone rubber or polyurethane and the like. Desirably the tubing is sealed to the needle hub using an adhesive. Conventionally the tubing will carry at its proximal end a means for connection to the source of infusion fluid. Commonly this connector is a female luer. Conventionally the tubing may also carry a pinch clip or Halkey Roberts clamp as a means for shutting off the flow of fluid.

The preferred intravenous needle assemblies of the present invention may be manufactured by simple assembly of the component parts namely (a) the needle hub is insert moulded around the pointed needle (b) the body portion, wing section and horns are injection moulded as a single component (c) the body portion is placed onto the needle hub and is held against the annular flange (d) the tubing is then sealed onto the proximal end of the needle hub thereby holding the body portion on the needle hub. A protective sleeve is placed over the pointed needle to form an interference fit on the needle hub. The pinch clip and luer connection are fitted to the tubing. The whole assembly may then be sealed into a package and sterilised by exposure to ethylene oxide or gamma-irradiation.

The intravenous needle assemblies are used in dialysis for the removal and return of the blood to the vein, infusion of other fluids containing nutrients, medicaments and the like. The needle is expected to remain within the vein for 4 to 6 hours. The intravenous assembly is aptly held in place on the skin using adhesive tape which is placed over the wing portions. Less desirably an adhesive film may be coated on to the lower surface of the wing portions and then covered by a protector strip until the assembly is required to be stuck in place. The protector strip is removed and the wing portions adhered to the skin.

From the foregoing it will be clear that the invention also comprises a sterile intravenous needle assembly when sealed in a package.

A preferred embodiment of the invention will now be described by way of example only, and with reference to the accompanying drawings wherein.

Figure 1:
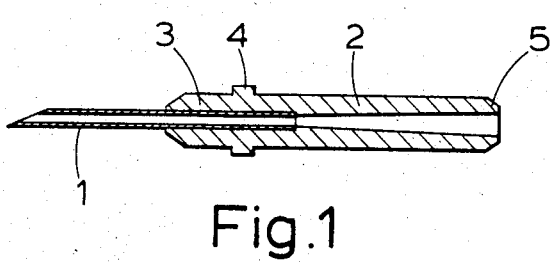
FIG. 1 is a cross-section of the needle and needle hub.

The needle and needle hub shown in FIG. 1 comprises a stainless steel needle (1) having a pointed end, the other end of which is held fixedly in a needle hub (2). The distal end of the needle hub (3) is of such dimensions as to form an interference fit outside a needle protector tube (not shown) which protects the needle from contamination prior to use. The annular flange (4) provides a stop against which the body portion rests. The proximal end of the needle hub (5) is of such dimensions as to fit inside the tubing leading from the source of infusion fluid. This tubing is adhered to the needle hub, it being a further advantage of using polyolefin for the body portion, that the body portion is not affected by the adhesive and mutual rotation of the body portion and needle hub is not impaired. The bores of the needle hub and needle are so arranged that a smooth connection is made between the two.

Figure 2:
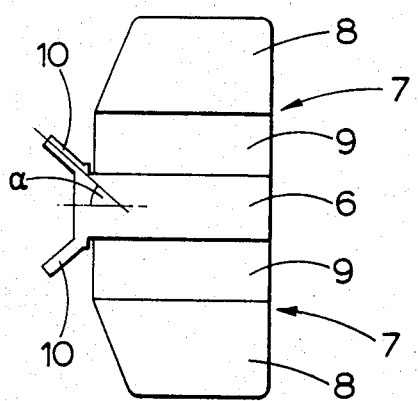
FIG. 2 is a view from above of the body portion, wing section and horns.

The second component of the assembly is shown in FIG. 2 comprising a body portion (6) having oppositely extending wing sections (7). The wing sections (7) are formed with thicker (8) and thinner areas (9) which are shown more clearly in FIG. 3. The horns (10) are shown extending forward from the wing sections (7) and away from the body portion (6). The angle between the direction of the horns (10) and the axis of the needle is shown in this figure as α, and is conventionally 30° to 60°, for example 45°.

Figure 3:
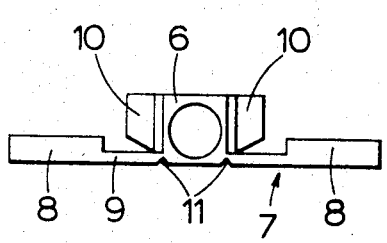
FIG. 3 is an end view looking from the right hand end of FIG. 2.

An end view of the body portion (6), wing section (7) and horns (10) is shown in FIG. 3 as viewed from the right hand side of FIG. 2. The thicker (8) and thinner (9) areas of the wing section are shown. The thinner areas (9) being of such dimensions that they will close around the body portion (6) when the wing sections are folded. The wing sections fold on a hinge portion (11).

Figure 4:
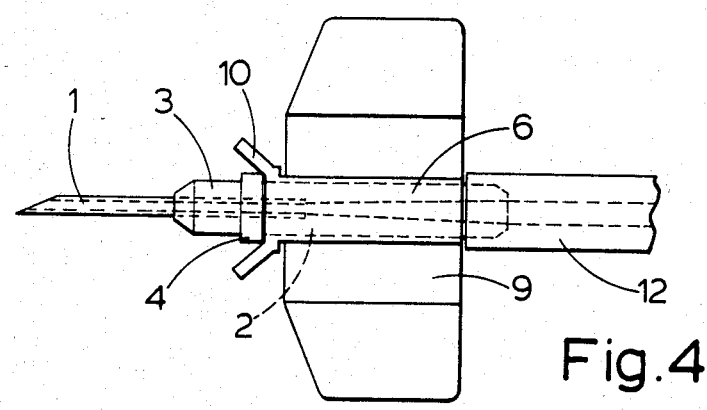
FIG. 4 is a view from above of the complete intravenous needle assembly.

A complete intravenous needle assembly is shown in FIG. 4, the needle hub (2) being free to rotate inside the body portion (6). The body portion being held in place between the annular flange (4) and the tubing (12) adhered to the proximal end of the needle hub. The tubing (12) may carry at its other end a female luer lock connector and centrally on the tubing a pinch clip whereby the flow of infusion fluid may be closed off. It is a considerable advantage in placing the needle if the distal end of the needle hub (3) carries a mark which designates the attitude of the bevel of the pointed needle. This mark may take the form of a coloured dot or indented portion on the needle hub.

Figure 5:
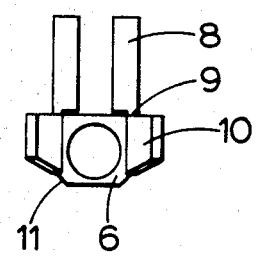
FIG. 5 is an end view of FIG. 2 from the left hand end showing the wing sections folded.

FIG. 5 shows an end view of the body portion (6) with the wing sections folded as viewed from the left hand side of FIG. 2. This shows how the thinner areas of the wing sections are arranged to close around the square body portion (6) in such a way that there is a gap between the two thicker areas (8) whereby they do not interlock or co-operate with each other in any way. Suitably the outer surfaces of the thicker areas of the wing sections may carry a raised pattern to assist gripping the wings when folded.

Figure 6:
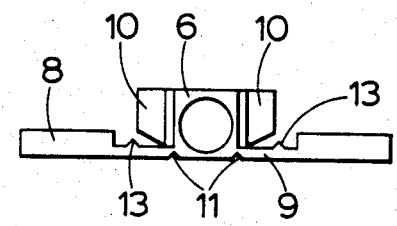
FIG. 6 shows an end view of an alternative embodiment of the handle with a raised portion in the thinner area of the wing.

An end view of the body portion (6), wing section (7) and horns (10) is shown in FIG. 6 in a similar manner to that shown in FIG. 3. The thicker (8) and thinner (9) areas of the wing section are shown. The thinner areas (9) in this embodiment show a raised portion (13) in the form of a rib which runs along the thinner area of the wing section in a direction parallel to the needle axis. The thinner areas (9) being of such dimensions that they will close around the body portion (6) when the wing sections are folded. The wing sections fold at a hinge portion (11).

Figure 7:
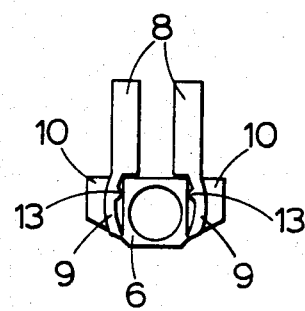
FIG. 7 shows the embodiment of FIG. 6 with the wings in the folded position.

FIG. 7 shows the embodiment of FIG. 6 with the wing areas (7) folded around the body portion (6). The raised portions (13) provide sufficient pressure against the body portion to prevent rotation of the needle hub during the insertion operation. The dimensions of the thinner areas (9) are such that the thicker areas come together as shown on top of the body portion (6).

What is claimed is:

1. A handle for use in an intravenous needle assembly for placing and maintaining an intravascular needle within a vein which comprises a body portion being connected via hinge portions to oppositely extending wing sections, in which said body portion has at its distal end an insertion aid in the form of a pair of laterally extending horns aginst which pressure may be applied when introducing the point of the needle beneath the skin and in which each of said wing portions of the handle has adjacent to the hinge a thinner portion having dimensions such that when the wings are folded the thinner portion conforms to and folds around the body portion in close fit therewith, each of said thinner portions carries a raised area on the surface which in use contacts the body portion when the wings are folded so as to apply pressure to the body portion.

2. An intravenous needle assembly for placing and maintaining an intravascular needle within a vein which assembly comprises
   (a) a needle
   (b) a hub which rigidly holds the needle and
   (c) a handle which is mounted on the hub in a manner which allows free rotation of the hub within the handle, in which said handle comprises a body portion connected via hinge portions to oppositely extending wing sections in which said body portion has at its distal end an insertion aid in the form of a pair of laterally extending horns against which pressure may be applied when introducing the point of the needle beneath the skin and in which the wing sections have thinner portions in which thinner portion carries a raised area which applies pressure to the body portion when the wings are folded thereby preventing rotation of the needle hub.

* * * * *